United States Patent [19]
Doggett, Jr.

[11] Patent Number: 5,871,153
[45] Date of Patent: Feb. 16, 1999

[54] DISINFECTANT DISPENSING AND FRAGRANCE DIFFUSING APPARATUS

[75] Inventor: John H Doggett, Jr., Memphis, Tenn.

[73] Assignee: Auto-San, Inc., Memphis, Tenn.

[21] Appl. No.: 886,111

[22] Filed: Jun. 30, 1997

[51] Int. Cl.⁶ .................................................. A24F 25/00
[52] U.S. Cl. ................................ 239/34; 239/44; 239/47; 239/57
[58] Field of Search .................................... 239/34, 37, 38, 239/44, 47, 51.5, 57, 145; 4/228.1

[56]         References Cited

U.S. PATENT DOCUMENTS

| | | | |
|---|---|---|---|
| 660,543 | 10/1900 | Freese . | |
| 957,449 | 5/1910 | Walz . | |
| 1,009,205 | 11/1911 | Winter . | |
| 1,063,684 | 6/1913 | Hitchcock . | |
| 1,171,737 | 2/1916 | Madigan . | |
| 1,751,257 | 3/1930 | Vallebuona | 239/34 |
| 2,177,056 | 10/1939 | Crowell | 299/23 |
| 2,251,734 | 8/1941 | Fuld et al. | 261/103 |
| 2,537,357 | 1/1951 | Levin | 239/47 |
| 2,687,916 | 8/1954 | Reynolds | 299/22 |
| 2,806,315 | 9/1957 | Kalensky | 239/48 |
| 3,254,841 | 6/1966 | Loncker, Sr. | 239/42 |
| 4,229,415 | 10/1980 | Bryson | 19/0 |
| 4,610,394 | 9/1986 | Bryson | 239/57 |
| 4,830,791 | 5/1989 | Muderlak et al. | 239/57 |
| 4,931,258 | 6/1990 | Zlotnik et al. | 239/57 |
| 5,529,216 | 6/1996 | Klima et al. | 222/130 |
| 5,544,682 | 8/1996 | McDaniel | 141/9 |

*Primary Examiner*—Andres Kashnikow
*Assistant Examiner*—Lisa Ann Douglas
*Attorney, Agent, or Firm*—Walker, McKenzie & Walker, P.C.

[57]              ABSTRACT

An improved disinfectant dispensing and fragrance diffusing apparatus for dispensing a liquid disinfectant. The disinfectant dispensing and fragrance diffusing apparatus has a first portion including a container and a delivery mechanism. The container is for holding the liquid disinfectant, and the delivery mechanism is for delivering the liquid disinfectant from the container into a toilet bowl or urinal. The improvement comprises a second portion including at least one object having a particular fragrance and an attachment mechanism for removably attaching the object to the first portion. The attachment mechanism can removably attach more than one object to the first portion so that the intensity of the particular fragrance can be varied. The particular fragrance is diffused into the air adjacent the toilet bowl or urinal.

9 Claims, 4 Drawing Sheets

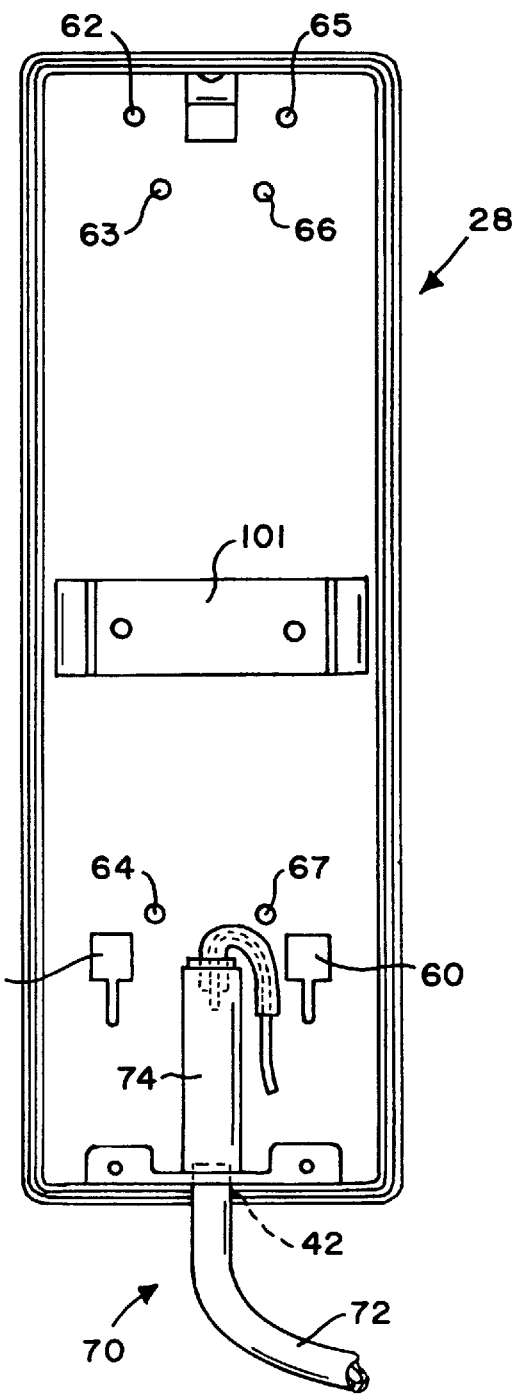

DISINFECTANT DISPENSING AND FRAGRANCE DIFFUSING APPARATUS

CROSS REFERENCE TO RELATED APPLICATIONS

Not applicable.

STATEMENT REGARDING FEDERALLY SPONSORED RESEARCH OR DEVELOPMENT

Not applicable.

REFERENCE TO A "MICROFICHE APPENDIX"

Not applicable.

BACKGROUND OF THE INVENTION

1. Field of the Invention

The present invention relates, in general, to public bathroom disinfectants and deodorizers, and in particular, to an apparatus which disinfects a public toilet or urinal and deodorizes the surrounding area.

2. Information Disclosure Statement

It is often desired to provide an apparatus which will disinfect a public toilet or urinal and which will deodorize the surrounding area. Well-known solutions for this problem include providing an apparatus which will dispense drips of a liquid disinfectant into the public toilet or urinal. The liquid disinfectant also includes a fragrance and the apparatus diffuses this fragrance into the surrounding area. Operators of public bathroom facilities often desire the option of choosing between many different fragrances so that the fragrance of the surrounding area will be comfortable and pleasing to users of the public bathroom. Well known solutions for this problem include manufacturing liquid disinfectants having different fragrances so that the public bathroom operator can choose a liquid disinfectant having a particular fragrance that appears to be pleasing. It is burdensome to produce and distribute these multiple liquid disinfectants. Another problem with this solution is that it does not give the public bathroom operator the ability to vary the intensity of a particular fragrance being diffused by the apparatus. An additional problem occurs when the public bathroom operator decides that the chosen fragrance is undesirable and wishes to choose a new fragrance. The public bathroom operator must wait until the entire amount of the remaining liquid disinfectant is used by the apparatus, or to immediately change the fragrance, must replace the remaining amount of the liquid disinfectant with another liquid disinfectant having a different fragrance. This is inefficient and inconvenient to the public bathroom operator.

It is therefore desirable to have an improved disinfectant dispensing and fragrance diffusing apparatus that will enable the particular fragrance and the intensity of the particular fragrance being diffused to be changed independently of the liquid disinfectant being dispensed.

The following patents, some of which may be relevant to the present invention: Freese, U.S. Pat. No. 660,543, issued Oct. 23, 1900; Walz, U.S. Pat. No. 957,449, issued May 10, 1910; Winter, U.S. Pat. No. 1,009,205, issued Nov. 21, 1911; Hitchcock, U.S. Pat. No. 1,063,684, issued Jun. 3, 1913; Fuld et al., U.S. Pat. No. 2,251,734, issued Aug. 5, 1941; Loncker, U.S. Pat. No. 3,254,841; and Byrson, U.S. Pat. No. 4,229,415, issued Oct. 21, 1980.

Additionally, the inventors are aware of Madigan, U.S. Pat. No. 1,171,737, issued Feb. 15, 1916; Crowel, U.S. Pat. No. 2,177,056, issued Oct. 24, 1939; and Reynolds, U.S. Pat. No. 2,687,916, issued Aug. 31, 1954, which may be relevant to the present invention. None of these references, either singly or in combination, disclose or suggest the present invention.

BRIEF SUMMARY OF THE INVENTION

The present invention is an improved disinfectant dispensing and fragrance diffusing apparatus for dispensing a liquid disinfectant. The disinfectant dispensing and fragrance diffusing apparatus has a first portion having a container for holding the liquid disinfectant and delivery means for delivering the liquid disinfectant from the container. The improvement comprises a second portion including at least one object having a particular fragrance and attaching means for removably attaching the object to the first portion.

It is an object of the present invention to provide a number of different objects, where each object has its own particular fragrance. The diffused fragrance can be varied depending upon the particular fragrant object chosen for attachment to the first portion.

It is an object of the present invention to provide attachment means for removably attaching at least one object to the first portion. The intensity of the diffused fragrance can be increased by removably attaching more than one object having the same particular fragrance to the first portion.

BRIEF DESCRIPTION OF THE SEVERAL VIEWS OF THE DRAWING

FIG. 4 is a rear elevational view of the reservoir tray.

FIG. 5 is a front elevational view of a back portion.

DETAILED DESCRIPTION OF THE INVENTION

Figure 1:
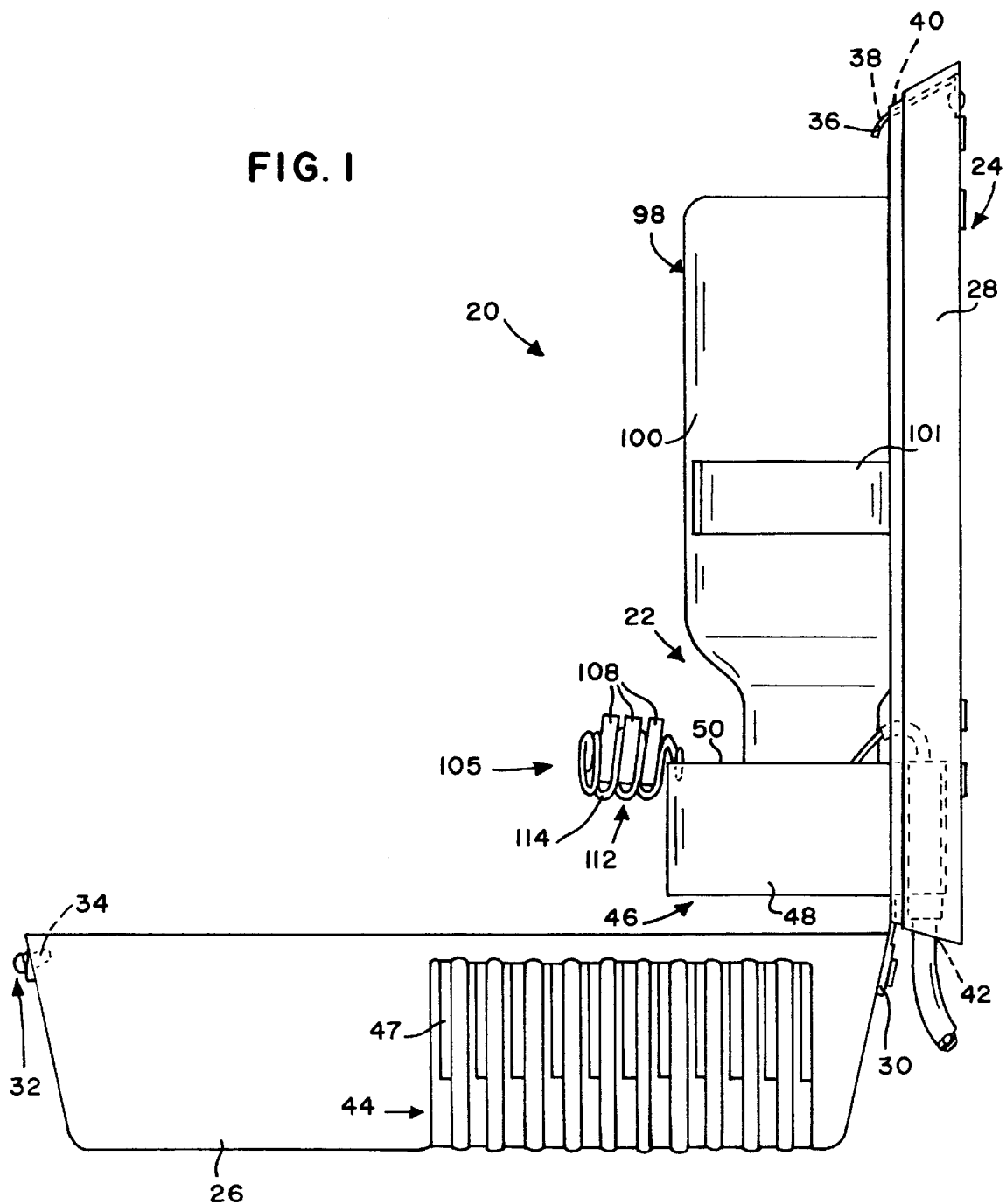
FIG. 1 is a side elevational view of the present invention shown with the enclosure in an opened position.
Figure 2:
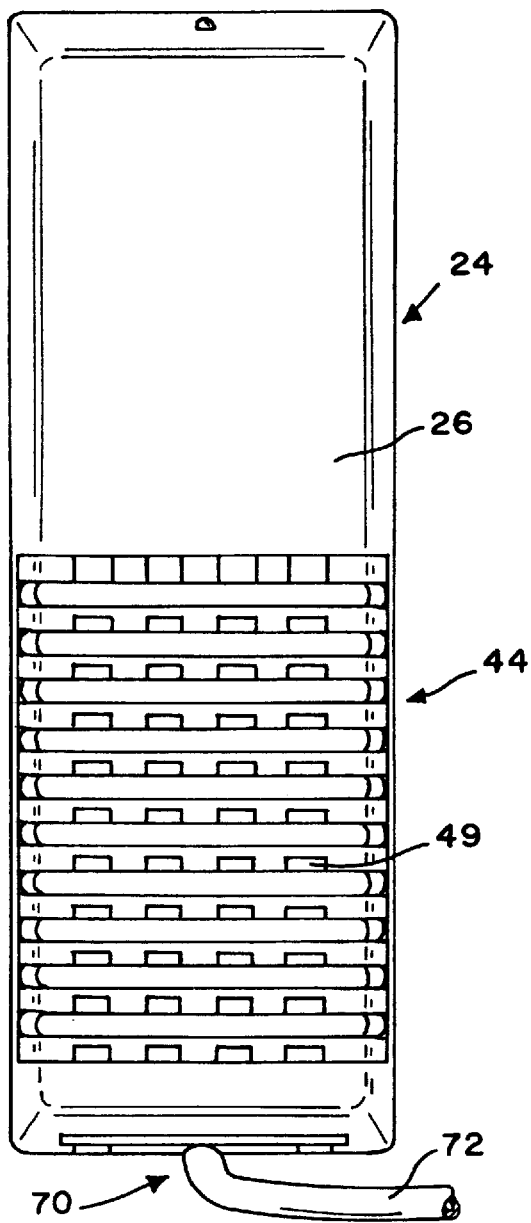
FIG. 2 is a front elevational view of the present invention.

Referring to FIGS. 1–8, the present invention is seen to comprise an improved disinfectant dispensing and fragrance diffusing apparatus 20 for dispensing a liquid disinfectant d. Referring to FIG. 1, which shows a side elevational view of the present invention, the disinfectant dispensing and fragrance diffusing apparatus 20 is seen to have a first portion 22 and an openable and closable retainer 24 for holding the first portion 22. The first portion 22 and the retainer 24 are well known in the art. The retainer 24 has a front portion 26 and a back portion 28 connected by a hinge 30 so that the retainer 24 is openable and closable. The front 26 and back 28 portions and the hinge 30 are preferably molded from a well known plastic material. The hinge 30 is attached to the front portion 26 using rivets and is attached to the back portion 28 using screws. A well known latch 32 is provided to releasably maintain the retainer 24 in the closed position. A suitable latch 32 may be constructed by including a pin 34 adjacent the top of the front portion 26 and by including a metal projection 36 adjacent the top of the back portion 28. The metal projection 36 has hole 38 therethrough to catch the pin 34. The back portion 28 has a slit 40 above the metal projection 36 so that a tool, such as a pencil tip, for example, can be placed through the slit 40 to push the metal projection 36 away from the pin 34, thus, causing the retainer 24 to open. The bottom of the back portion 28 has a tube aperture 42. The front portion 26 of the retainer 24 includes a plurality of diffusion apertures 44 preferably comprising side apertures 47 as shown in FIG. 1, and preferably comprising front apertures 49 as shown in FIG. 2, which shows a front elevational view of the present invention. The plurality of diffusion apertures 44 are preferably formed when the front portion 26 is molded as is well known in the art.

Figure 3:
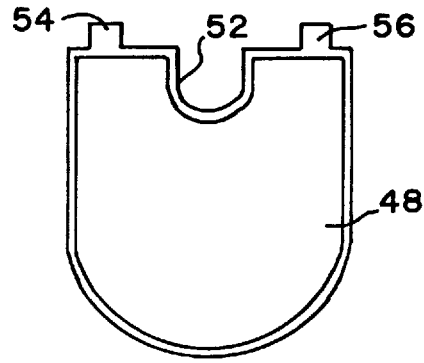
FIG. 3 is a top view of a reservoir tray.

Referring to FIG. 1, the first portion 22 has a container 46 for holding the liquid disinfectant d. The container 46 may comprise any well known means for holding a liquid, and the container 46 may be substantially open or substantially closed. The container 46 is seen to preferably comprise a reservoir tray 48 which has a top rim 50 and which is substantially open adjacent the top rim 50 of the reservoir tray 48. Referring to FIG. 3, which shows a top view of the reservoir tray 48, the reservoir tray 48 is seen to preferably have a groove 52 and a pair of well known male tabs 54, 56 which extend outwardly from the top rim 50. The male tabs 54, 56 then extend downwardly as can be seen in FIG. 4. FIG. 4 shows a rear elevational view of the reservoir tray 48 from which the groove 52 can also be seen.

Referring to FIG. 5, which shows a front elevational view of the back portion 28, the back portion 28 is seen to include a pair of support slots 58, 60 for engaging the pair of male tabs 54, 56 (shown in FIG. 3) and for supporting the reservoir tray 48 (as shown in FIG. 1). The back portion 28 also has a plurality of attachment holes 62, 63, 64, 65, 66, 67 for receiving screws to attach the back portion 28 to a wall.

Figure 6:
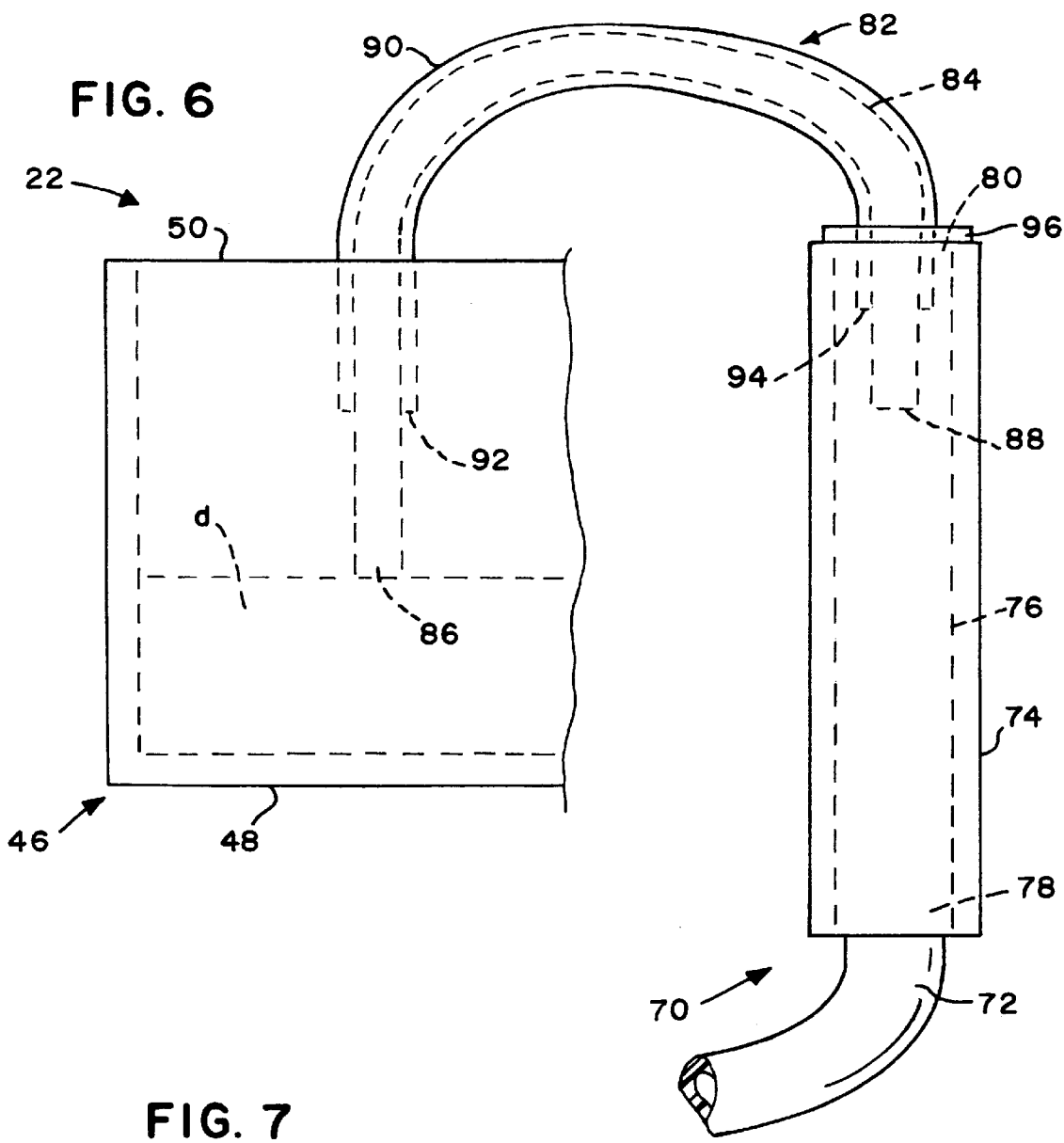
FIG. 6 is an enlarged side elevational view of a portion of the reservoir tray so that delivery means and drip means can be seen.

The first portion 22 also has well known delivery means 70 for delivering the liquid disinfectant d from the container 46 to a toilet or urinal. Delivery means 70 may simply comprise a hole in the container 46 that allows the liquid disinfectant d to flow to a toilet or urinal. Delivery means 70 may additionally or alternatively comprise a tube 72. Referring to FIG. 5, delivery means 70 preferably alternatively comprises a tube 72. The tube 72 preferably extends through the tube aperture 42. Referring to FIG. 6, which shows an enlarged elevational side view, the tube 72 preferably includes a barrel 74 having a barrel bore 76 therethrough. A first end 78 of the barrel bore 76 sealingly communicates with the tube 72. The length of the barrel 74 is preferably sized so that when the bottom of the barrel 74 is positioned immediately above the tube aperture 42, (as shown in FIG. 5), a second end 80 of the barrel bore 76 is positioned adjacent the top rim 50 of the reservoir tray 48.

Referring generally to FIGS. 3 and 5, it will now be apparent that the purpose of the groove 52 is to secure the barrel 74 adjacent the reservoir tray 48. Referring to FIG. 6, the first portion 22 preferably also has drip means 82 for communicating with the liquid disinfectant d in the container 46 and for providing drips of the liquid disinfectant d to delivery means 70 . Drip means 82 preferably includes a wick 84 having a first wick end 86 and a second wick end 88. The first wick end 86 is preferably positioned approximately even with the height of the liquid disinfectant d in the container 46, and the second wick end 88 is preferably positioned to communicate with delivery means 70. Drip means 82 preferably includes a flexible J-tube 90.

Referring to FIG. 6, the J-tube 90 has a first J-tube end 92 and a second J-tube end 94. The J-tube 90 includes a washer 96 being adjustably secured against the J-tube 90 adjacent the second J-tube end 94. The second J-tube end 94 is placed within the second end 80 of the barrel bore 76 and the washer 96 supports the J-tube 90 by resting on the top of the barrel 74. The wick 84 is placed through the J-tube 90 so that it extends through the first J-tube end 92 and preferably through the second J-tube end 94. The vertical height of the first wick end 86 can be adjusted to a desired level by adjusting the point at which the washer 96 is secured against the J-tube 90. It is well known in the art that the drip rate can be increased by extending the first wick end 86 further into the liquid disinfectant d. To obtain a preferred slow drip rate the washer 96 is preferably adjusted so that the vertical height of the first wick end 86 is positioned approximately even with the height of the liquid disinfectant d in the container 46.

Figure 7:
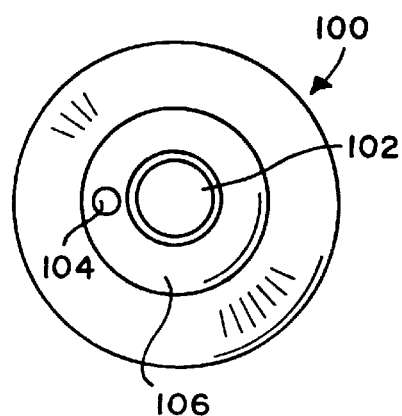
FIG. 7 is a bottom elevational view of a bottle.

Referring to FIG. 1, the first portion 22 preferably has a receptacle 98 being disposed above the container 46. The receptacle 98 is for supplying the liquid disinfectant d to the container 46. The receptacle 98 preferably comprises a bottle 100 molded from a well known plastic material. Referring to FIG. 7, which shows a bottom elevational view, the bottle 100 is seen to have a mouth 102 and a pressure equalization hole 104 extending through a bottle shoulder 106. Referring to FIG. 1, the bottle 100 is secured to the back portion 28 of the retainer 24 using means well known in the art, such as bracket 101, for example. The bottle 100 is positioned so that the mouth 102 (not shown in FIG. 1) and the equalization hole 104 (not shown in FIG. 1) are located below the top rim 50 of the reservoir tray 48. The mouth 102 and the equalization hole 104 cooperate in a manner well known in the art to maintain a constant level of liquid disinfectant d within the reservoir tray 48. While maintained at this constant level, the liquid disinfectant d will be delivered to a toilet or urinal. When there is not enough liquid disinfectant d remaining in the bottle 100 to maintain the constant level of the liquid disinfectant d within the reservoir tray 48, the liquid disinfectant d will cease to be delivered to the toilet or urinal, and the bottle 100 will have to be refilled or replaced with a full bottle of liquid disinfectant.

Every element of the present invention that has been previously described is well known in the art. Prior art disinfectant dispensing and fragrance diffusing apparatus used a liquid disinfectant which also included a fragrance, and this fragrance was diffused into the surrounding area. Prior art liquid disinfectants were manufactured with different fragrances so that the fragrance diffused by the prior art disinfectant dispensing and fragrance diffusing apparatus could be changed by changing the liquid disinfectant to one that included a different fragrance. This fragrance typically was oil based and the oil reduced the durability of the wick. When a public bathroom operator was displeased with the diffused fragrance, the public bathroom operator had to wait until the entire amount of the remaining liquid disinfectant was utilized by the apparatus, or to immediately change the diffused fragrance, had to replace the remaining amount of the liquid disinfectant with another liquid disinfectant having a different fragrance.

The improvement of the present invention provides the public bathroom operator with the ability to change, independently of the liquid disinfectant d, the particular fragrance being diffused and the intensity of the particular fragrance being diffused. The liquid disinfectant d is no longer the source of the diffused fragrance so the liquid disinfectant d is preferably manufactured without adding an additional fragrance.

Referring to FIG. 1, the improvement is seen to comprise a second portion 105. The second portion 105 includes at least one object 108 having a particular fragrance, and may comprise a plurality of objects 108 having a particular fragrance. The intensity of the particular fragrance can be varied by varying the number of objects 108 included with the second portion 105. It should be understood that each one of the objects 108 included with the second portion 105 at a given time will preferably have the same particular fragrance. Preferably, the number of objects 108 can be varied between one and three to vary the intensity of the particular fragrance. For, example, one object 108 having a particular fragrance can be included with the second portion 105 to diffuse a mild intensity of the fragrance. As another example, two objects 108 having the same particular fragrance can be included with the second portion 105 to diffuse a medium intensity of the fragrance. As a last example, three objects 108 having the same particular fragrance can be included with the second portion 105 to diffuse a high intensity of the fragrance. These one, two or three objects 108 may be considered as a set of objects 108 having a particular fragrance. Many sets of objects 108 with each set having a different particular fragrance can be supplied so that a user of the present invention can choose between different particular fragrances. Thus, as is now apparent to those skilled in the art, both the particular fragrance and the intensity of the particular fragrance can immediately be varied without having to replace the remaining amount of the liquid disinfectant d with another liquid disinfectant d.

The plurality of objects 108 having a particular fragrance can be manufactured in any one of a number of well known shapes and in any one of a number of well known mediums. Each object 108 having a particular fragrance is preferably manufactured to have thin rectangular shape, defined as a wafer, having a length of approximately 2.25 inches (5.72 cm.), a width of approximately 1.25 inches (3.18 cm.), and a depth of approximately 0.25 inches (0.64 cm.). The preferable medium is synthetic felt. Unscented synthetic felt wafers are commercially available and for, example, can be obtained by Bacon Felt Company having a place of business at Tauntown, Massachusetts. A particular fragrance can then be added to the unscented synthetic felt wafer.

When the retainer 24 is closed, the plurality of diffusion apertures 44 allow the particular fragrance from the objects 108 inside of the retainer 24 to diffuse into the air in the surrounding area.

Figure 8:
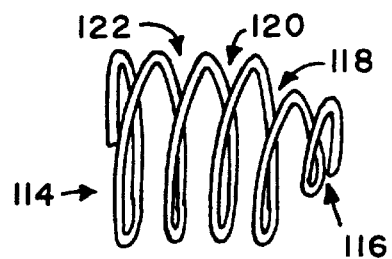
FIG. 8 is a side elevational view of a coiled spring.

Referring to FIG. 1, the second portion 105 is also seen to comprise attaching means 112 for removably attaching at least one object 108 to the first portion 22. Attaching means 112 is preferably for removably attaching a plurality of objects 108 to the first portion 22. Attaching means 112 preferably comprises a coiled spring 114 having a plurality of adjacent coils. The plurality of objects 108 are held between different ones of the adjacent coils. The coiled spring 114 is preferably attached to the container 46 by sliding two adjacent coils over the top rim 50 of the container 46. Referring to FIG. 8, which shows an enlarged side view of the coiled spring 114, a first space 116 between adjacent coils is used to attach the coiled spring 114 to the container 46 (as shown in FIG. 1). An object 108 having a particular fragrance can be secured between adjacent coils. An object 108 is preferably secured between adjacent coils in the second space 118, the third space 120, or the fourth space 122. It being understood that an object 108 can be secured in the second space 118, another object can be secured in the third space 120, and still another object can be secured in the fourth space 122. Attaching means 112 may comprise any of a number of means for attaching at least one object 108 to the first portion 22, as will now be apparent to those skilled in the art. Examples include baskets, trays, clips, slots, and other well known means.

Although the present invention has been described and illustrated with respect to a preferred embodiment and a preferred use therefor, it is not to be so limited since modifications and changes can be made therein which are within the full intended scope of the invention.

We claim:

1. An improved disinfectant dispensing and fragrance diffusing apparatus for dispensing a liquid disinfectant, the disinfectant dispensing and fragrance diffusing apparatus having a first portion having:

(a) a container for holding the liquid disinfectant; and
    (b) delivery means for delivering the liquid disinfectant from the container;

wherein the improvement comprises a second portion including:

(c) at least one object having a particular fragrance; and
    (d) attaching means for removably attaching said at least one object to first portion, said attaching means comprising a coiled spring.

2. An improved disinfectant dispensing and fragrance diffusing apparatus for dispensing a liquid disinfectant, the disinfectant dispensing and fragrance diffusing apparatus having a first portion having:

(a) a container for holding the liquid disinfectant; and
    (b) delivery means for delivering the liquid disinfectant from the container;

wherein the improvement comprises a second portion including:

(c) a plurality of objects each having a same particular fragrance; and
    (d) attaching means for removably attaching said plurality of objects to the first portion, said attaching means comprising a coiled spring.

3. The improved disinfectant dispensing and fragrance diffusing apparatus for dispensing a liquid disinfectant as recited in claim 2, in which said coiled spring is attached to the container.

4. An improved disinfectant dispensing and fragrance diffusing apparatus for dispensing a liquid disinfectant, the disinfectant dispensing and fragrance diffusing apparatus having a first portion having:

(a) a container for holding the liquid disinfectant;
    (b) a receptacle being disposed above the container, the receptacle for supplying the liquid disinfectant to the container;
    (c) delivery means for delivering the liquid disinfectant from the container; and
    (d) drip means for communicating with the liquid disinfectant in the container and for providing drips of the liquid disinfectant to the delivery means;

wherein the improvement comprises a second portion including:

(e) at least one object having a particular fragrance; and
    (f) attaching means for removably attaching said at least one object to the first portion.

5. The improved disinfectant dispensing and fragrance diffusing apparatus for dispensing a liquid disinfectant as recited in claim 4, in which said attaching means comprises a coiled spring.

6. The improved disinfectant dispensing and fragrance diffusing apparatus for dispensing a liquid disinfectant as recited in claim 4, in which said attaching means is for removably attaching a plurality of objects to the first portion, each one of said plurality of objects having the same particular fragrance.

7. The improved disinfectant dispensing and fragrance diffusing apparatus for dispensing a liquid disinfectant as recited in claim 6, in which said attaching means comprises a coiled spring.

8. The improved disinfectant dispensing and fragrance diffusing apparatus for dispensing a liquid disinfectant as recited in claim 7, in which said coiled spring is attached to the container.

9. An improved disinfectant dispensing and fragrance diffusing apparatus for dispensing a liquid disinfectant, the disinfectant dispensing and fragrance diffusing apparatus having a first portion having:

(a) a container for containing the liquid disinfectant;

(b) a receptacle being disposed above the container, the receptacle for supplying the liquid disinfectant to the container;

(c) delivery means for delivering the liquid disinfectant from the container; and (d) drip means for communicating with the liquid disinfectant in the container and for providing drips of the liquid disinfectant to the delivery means;

the disinfectant dispensing and fragrance diffusing apparatus further having an openable and closable retainer for holding the first portion;

wherein the improvement comprises a second portion including:

(f) a plurality of objects having a particular fragrance, each one of said plurality of objects having the same particular fragrance; and (g) a spring having a plurality of adjacent coils, said plurality of objects being held between different ones of said adjacent coils, said spring being attached to the container.

* * * * *